United States Patent
Mehta

[11] Patent Number: 5,871,776
[45] Date of Patent: Feb. 16, 1999

[54] CONTROLLED-RELEASE NIFEDIPINE

[76] Inventor: Atul M. Mehta, 252 E. Crescent Ave., Ramsey, N.J. 07446

[21] Appl. No.: 738,925

[22] Filed: Oct. 28, 1996

[51] Int. Cl.[6] ............................... A61K 9/16; A61K 9/58
[52] U.S. Cl. ..................... 424/462; 424/497; 514/356; 514/964
[58] Field of Search .................... 424/497, 462, 424/451, 457, 458, 459, 464, 468, 489, 490; 514/356, 964, 975

[56] References Cited

U.S. PATENT DOCUMENTS

| | | | |
|---|---|---|---|
| 4,765,990 | 8/1988 | Sugimoto et al. | 424/494 |
| 4,814,175 | 3/1989 | Tack et al. | 424/453 |
| 4,874,613 | 10/1989 | Hsaio | 424/458 |
| 4,900,557 | 2/1990 | Dell et al. | 424/452 |
| 5,145,683 | 9/1992 | Rhodes | 424/451 |
| 5,204,121 | 4/1993 | Buecheler et al. | |
| 5,258,186 | 11/1993 | Ohmura | 424/497 |
| 5,286,493 | 2/1994 | Oshlack et al. | 424/468 |
| 5,292,461 | 3/1994 | Juch et al. | 264/37 |
| 5,496,561 | 3/1996 | Okada et al. | |
| 5,543,154 | 8/1996 | Rork et al. | 424/473 |
| 5,567,441 | 10/1996 | Chen | 424/494 |
| 5,594,013 | 1/1997 | Trigger | 514/356 |

FOREIGN PATENT DOCUMENTS

| | | |
|---|---|---|
| 0 386 440 | 12/1990 | European Pat. Off. |
| 0 514 568 | 11/1992 | European Pat. Off. |

*Primary Examiner*—Robert H. Harrison
*Attorney, Agent, or Firm*—Kenyon & Kenyon

[57] ABSTRACT

A nifedipine formulation for oral administration is described that provides controlled, constant release of the pharmaceutical for about twenty four hours after a short delay following oral administration. There is also provided a method for preparing a controlled release formulation of nifedipine, which method includes coating pellets with multiple nifedipine-containing layers, along with an outer controlled release coating comprised of a water permeable polymer and lubricant/glidant. The pellets are then cured at an elevated temperature over several days. A method of using the formulations of the present invention for the treatment of patients is also described.

19 Claims, 4 Drawing Sheets

CONTROLLED-RELEASE NIFEDIPINE

This application claims the benefit of U.S. Provisional application Ser. No. 60/008,180 filed Oct. 31, 1995.

FIELD OF THE INVENTION

This invention relates to novel oral pharmaceutical formulations of nifedipine having controlled release properties, and also a method of preparing such formulations. The formulations are comprised of pellets having multiple coatings, the innermost layers from which nifedipine is slowly released over time. These formulations have been shown to exhibit excellent controlled release properties. The method for preparing the formulations provides pharmaceutical preparations for oral administration in both tablet and capsule dosage form, and, more particularly, provides therapeutic preparations comprising coated pellets which release a dose of nifedipine over a prolonged period of time in the digestive system of a patient.

BACKGROUND OF THE INVENTION

It has long been known that almost all pharmacologically active compounds are most effective when present in the blood plasma within a certain concentration range. Above this range, there sometimes may be a danger of deleterious side effects. Also, excess drug in the blood plasma may be wasted if the concentration is significantly above the blood level that results in the maximum pharmacological effect, thus making both the manufacture and use of the drug formulation unnecessarily costly. Alternatively, when the concentration of drug in the plasma is below the most effective range, there is the danger that the active ingredient may not be maximally effective, or may not be effective at all.

When physiologically possible, an oral dosage form is the preferred route of administration of most pharmaceutical compounds because it provides easy, low cost administration. However, patient compliance is an important factor to consider in conjunction with oral administration of a pharmaceutical compound, especially if the compound must be taken three or four times a day. To maximize patient compliance, it is desirable to reduce the number of daily dosage units a patient must take to attain effective therapy. The use of fewer, longer acting dosages also improves the constancy of drug concentrations in the blood over time, and since the drug can be closer to its ideal therapeutic dosage throughout the day, this may result in improved therapy.

Nifedipine (3,5-pyridinedicarboxylic acid, 1,4-dihydro-2, 6-dimethyl-4-(2-nitrophenyl)-, dimethyl ester) is a calcium channel antagonist which has been successfully used in the treatment of coronary artery spasms and hypertension. The administration of nifedipine in traditional capsule or tablet form requires the patient to remember to ingest tablets or capsules several times per day in order to maintain effective blood levels of the drug. In addition, many patients being treated on this drug regimen must take several other capsules or tablets for the treatment of other conditions or disease states, requiring a large total number of pills to be taken daily. Moreover, the administration of the drug several times per day results in non-constant blood levels throughout the day. Accordingly, it is important for the convenience of the patient, and to ensure dosage compliance, that the frequency of administration of nifedipine be kept to a minimum. It is also important that the level of nifedipine maintained in the blood plasma of a patient be relatively constant within the effective dosage range for the entire dosage period.

One method of accomplishing these goals is the use of controlled release formulations, some of which are well known in the prior art. Some controlled release formulations are comprised of a solid polymeric matrix throughout which a pharmaceutical compound has been dispersed. After the formulation is ingested, the active pharmaceutical compound slowly releases from the polymer matrix, resulting in prolonged release of the active ingredient.

Another method for achieving controlled release of a pharmaceutical agent relies on an osmotic pressure mechanism. European patent No. 0 386 440 A1, issued to Bayer AG, discloses nifedipine tablets having various specified surface areas in a controlled release, once daily formulation of nifedipine. The formulation releases nifedipine via an osmotic release mechanism; the diffusion of water into the tablet through a semi-permeable membrane causes pressure to build inside the tablet, which forces the drug out through a pinhole in the tablet coating. A controlled release tablet that releases nifedipine in this way is commercially available from Pfizer, Inc. under the trade name Procardia XL®, and this tablet has been found to give generally acceptable drug release profiles in vivo.

European Patent No. 0 5145683, issued to Ethical Pharmaceuticals, Inc., discloses a controlled release pharmaceutical composition comprising particles of a water-soluble material coated with microcrystalline particles of nifedipine and polyvinylpyrrolidone, the latter of which is present in an amount of from 10 to 90% by weight based on the weight of the nifedipine. The incorporation of polyvinylpyrrolidone in an amount less than that of the nifedipine is said to significantly slow the dissolution of nifedipine from the final dosage form.

Another approach to formulating controlled release compositions includes the dry blending of one or more polymer with the desired drug, forming a composition which, when exposed to fluid, forms a gel; the drug is then slowly released by diffusion from the gel.

Yet another approach to controlled release is the coating of small pellets (e.g., sugar beads or nonpareils) with the drug, followed by a coating with a barrier layer of some polymer which impedes the release of the drug into the liquid of the digestive system. Such small beads are often then packaged together to provide an oral dosage form, e.g., by placing the beads into a gelatin capsule.

The methods and formulations of the present invention use this latter approach, which heretofore has not successfully been applied to the controlled release delivery of nifedipine. The formulations of the present invention provide controlled release formulations in the form of pellets having multiple layers coated thereon, which provide for controlled release of the pharmaceutical agent from the individual pellets. The pellets may be then formulated into controlled release tablets or capsules. The controlled release of nifedipine from pellets prepared by the process of this invention maintains a constant blood level of nifedipine over a prolonged period of time. By using the methods of the present invention, it has been possible to prepare controlled release nifedipine formulations that have essentially the same in vitro drug release profiles (drug release as a function of time) as does Procardia XL®.

SUMMARY OF THE INVENTION

In one aspect of the present invention there is provided a controlled release formulation comprising a pharmaceutically effective amount of nifedipine comprising:

a non-pareil pellet having layered thereon (1) an innermost drug layer;

(2) a second drug layer, wherein each of said drug layers comprises a pharmaceutically acceptable binder agent and nifedipine at a ratio of about 0.5 to 5 binder agent to nifedipine weight/weight (w/w); and (3) an outermost controlled release coating comprising about 75 to about 80% of a water permeable polymer (w/w) based on the total weight of the outermost coating and about 20 to 25% lubricant/glidant agent, wherein the pellet is further comprised of a total amount of about 0.05 to about 5.0% surfactant (w/w) relative to the total amount of nifedipine present in the pellet.

In another aspect of the present invention there is provided a method of preparing a controlled release formulation comprising a pharmaceutically effective amount of nifedipine. The method includes the steps of:

A) applying to non-pareil pellets a suspension comprising a pharmaceutically acceptable binder agent and nifedipine at a ratio of about 0.5:5 (w/w) and, optionally, surfactant, to provide an innermost drug layer thereon;

B) applying to the pellets obtained in step (A) a second suspension comprising a pharmaceutically acceptable binder agent and nifedipine at a ratio of about 0.5:5 (w/w) and, optionally, surfactant to provide a second drug layer thereon;

C) applying to the pellets obtained in step (B) an aqueous dispersion comprising about 15 to about 20% of a water permeable polymer (w/w), about 3 to about 7% lubricant/glidant agent (w/w) and, optionally, surfactant to form an outermost controlled release coating; and D) curing the pellets obtained in step (C) at a temperature in the range of from about 30° to about 50° C. for about 2 to about 10 days, wherein the layered and coated pellets collectively are further comprised of a total amount of about 0.05 to about 5.0% surfactant (w/w) relative to the total amount of nifedipine present in the coated pellets.

In a preferred embodiment, the surfactant is localized in the innermost drug layer. In a most preferred embodiment of the invention, the controlled release formulation is prepared such that the innermost drug coating comprises about 1.25%–3.0% surfactant (w/w) based on the total amount of nifedipine in the pellets; and the controlled release coating comprises about 30% w/w calcium stearate and about 70% w/w polymer, to provide a nifedipine potency of about 40 to about 50%.

In yet another aspect of the invention there is provided a controlled release formulation prepared by the method set forth above.

DETAILED DESCRIPTION OF THE INVENTION

In one aspect, the present invention is directed to a method for preparing controlled release pharmaceutical products. There are essentially four general methods or principles used in the art to develop oral controlled release or controlled release dosage forms: (1) diffusion and/or dissolution control, (2) ion exchange, (3) repeat action, and (4) osmotic pressure. Each method has advantages and disadvantages. The present method for preparing controlled release formulations is primarily based on diffusion and/or dissolution control of the pharmaceutical agent.

The formulations of the present invention include pharmaceutically effective amounts of an active agent layered onto pellets in a multi-layered manner. The outermost layer of the pellets has a polymeric coating. Both the polymeric coating and the pharmaceutical containing layers may further comprise diluents, fillers and other pharmaceutical additives which may effect the rate of release of active agent(s) from the pellets.

The process for making the pharmaceutical formulations of the present invention includes forming a first layer of active agent on core pellets. In this first stage of forming the controlled release product, the pharmaceutical agent is layered onto the surface, e.g., of non-pareil or sugar and/or starch-based pellets in combination with a pharmaceutically acceptable binder agent and, optionally, a surfactant. In the second stage, the layered pellets produced in the first stage are layered with a mixture of the pharmaceutical agent, a pharmaceutically acceptable binder agent and, optionally, surfactant. In the third stage, the pellets are further coated with a controlled release coating mixture comprising a polymer, a lubricant/glidant agent and optionally, surfactant. The pellets prepared according to the above method are formulated to contain surfactant in at least one of the layers coated thereon. In a final stage of preparation, the pellets are cured at an elevated temperature for a substantially long period of time. Surprisingly, the resulting pellets exhibit approximately zero order release of the pharmaceutical agent and are storage stable for extended periods of time. After an approximately two hour delay following administration of the multi-layered pellets, there is a constant and controlled release of pharmaceutical agent within the effective dosage range.

The first stage in forming the controlled release formulations of the present invention includes forming a first layer on pellets with a mixture of the pharmaceutical agent, binder and, optionally, surfactant in a fluid bed apparatus.

Many types of pellets that would be suitable for use in the methods and formulations of the present invention are commercially available from a number of pharmaceutical supply companies; for example, non-pareils, sugar and/or starch-based pellets. Non-pareil pellets of particle size 25 to 30 mesh are particularly preferred, although any non-pareil pellet of mesh size within the range of 14 mesh to 60 mesh are also preferred for use in this invention.

The solvent used to form each of the first and second stage layers and the third stage coating mixtures may be any pharmaceutically acceptable solvent or mixture of acceptable solvents. Water, ethanol, or mixtures thereof are preferred solvents, although others can also be used.

Suitable binding agents for use in the present invention include, for example, hydroxypropylmethyl cellulose (3 to 6 cps, preferably 5 cps), hydroxyethyl cellulose, hydroxypropyl cellulose, methyl cellulose, vinyl pyrrolidone and the like. Preferably, hydroxypropylmethyl cellulose is used in the practice of the present invention. Preferably, the binder agent is dissolved in water to form a 5–30% (w/w) solution, preferably a 7–25% (w/w) solution and most preferably, an approximately 10% (w/w) solution.

The layering mixture for the first stage of the method of the present invention, then, preferably is a suspension composed of a binder agent in a pharmaceutically acceptable solvent, such as water, ethanol, or mixtures thereof. The first stage layering mixture also contains micronized pharmaceutical agent, such as, for example nifedipine or other active agent having physicochemical properties similar to nifedipine. The ratio of binder agent to pharmaceutical agent in the first stage layering mixture is about 0.5:5 (w/w), preferably about 1:4. Preferably, the first stage layer mixture comprises about one half the total unit dosage of pharmaceutical agent to be contained in the final, layered pellets.

Figure 3:
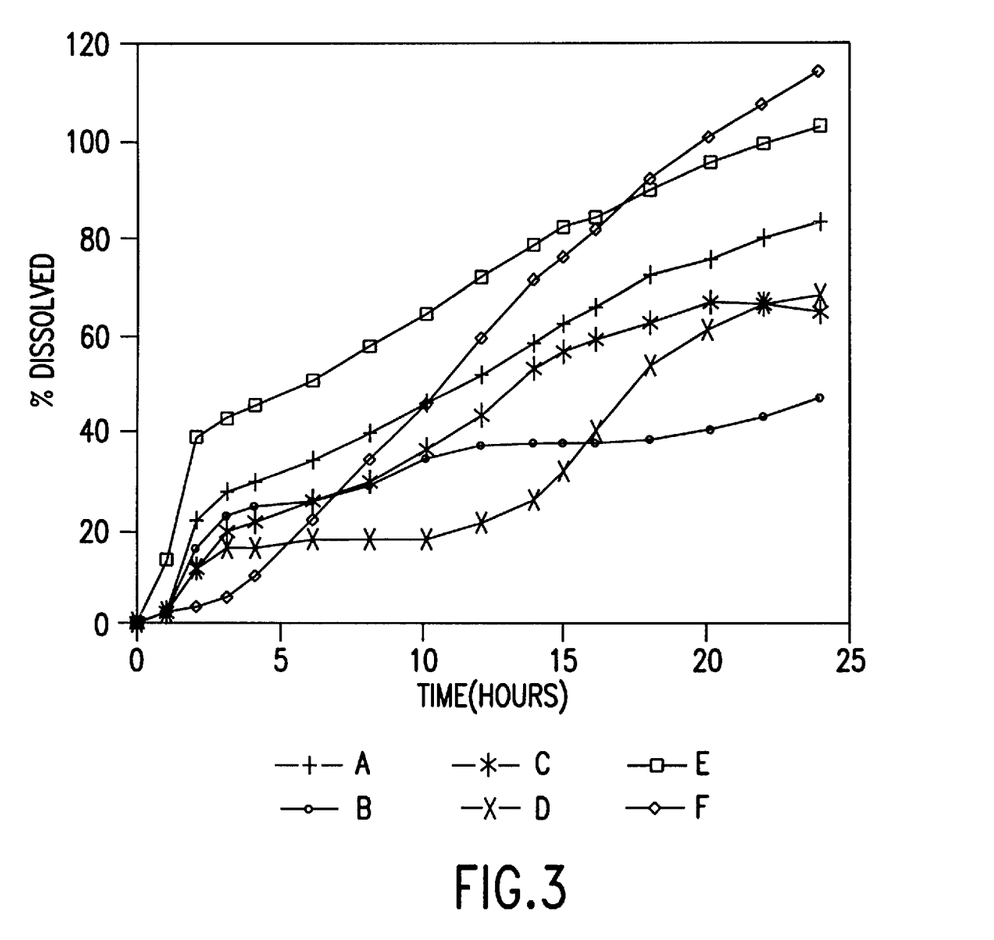
FIG. 3 is a graph of the in vitro release rate of nifedipine from pellets containing various amounts of surfactant at different locations within the coated pellet.

One or more ionic or non-ionic surfactants, such as sodium laurel sulfate, TWEEN® 20, TWEEN® 80 and the like may be added to the first stage layering mixture, at an amount of about 0.05–5% (w/w) based on the total amount of pharmaceutical agent present in the pellet. Preferably, the surfactant is present only in the innermost drug layer; and most preferably, is present in only the innermost drug layer in an amount of about 1.25%–3.0% (w/w) based on the total amount of pharmaceutical agent in the pellet. However, the surfactant may be present in either or both of the drug layers or throughout the layers and outermost coating of the pellet in a total amount in the range of from about 0.05% to about 3.0%, and preferably in a total amount of about 1.25%–3.0% (w/w) based on the total amount of pharmaceutical agent in the pellets. It is believed that the surfactant functions to ensure complete release of the pharmaceutical agent from the layer of the pellet in which it is located, as well as to provide the desired release rate, as shown in FIG. 3.

If desired, an antifoaming agent may also be added to the first stage layering mixture to aid in processing.

The first stage layering mixture is sprayed onto non-pareil or other pellets that have been suspended in a fluidized bed. Preferably, these pharmaceutical loaded pellets contain about one half the amount of pharmaceutical agent that will be ultimately contained in the final controlled release pellets. The first stage pellets contain, preferably, a concentration of about 7.5% w/w binder, based on the total weight of total pellet weight. After the pellets are layered, they may optionally be dried by air exposure or other methods known in the art (although drying may occur spontaneously from air flow in the fluid bed processor).

The pellets resulting from the first stage are then suspended in a fluidized bed apparatus, and are then sprayed with a second stage mixture containing the pharmaceutical agent and a binder agent in a solvent. The second stage coating mixture preferably does not contain surfactant. The ratio of binder agent to pharmaceutical agent in the second stage layering mixture is about 0.5:5 (w/w), and preferably, about 1:4. As with the first stage layering mixture, an antifoam agent may be added to the second stage layering mixture to aid in processing, if desired.

Preferably, the pharmaceutical loaded pellets of the first two stages of layering contain a total binder concentration of about 12.75% and provide in total a potency of approximately 50% (w/w) based upon the total weight of the layered pellets, although the potency can be adjusted as desired. When the pharmaceutical agent included in the first and second stage layerings is nifedipine, it is preferred that the pellet be formulated at about 45 to about 50% potency (w/w).

Pellets obtained from the second stage layering are then fluidized and sprayed with a controlled release outer coating, which constitutes the final layering stage of the method of the present invention. The controlled release coating contains a polymer that is water permeable, e.g., ethyl cellulose, a copolymer of acrylic and methylacrylic acid esters, such as EUDRAGIT® RL 30 D and RS 30D or a poly(meth)acrylate polymer, such as EUDRAGIT® NE 30 D, and combinations thereof. Most preferably, the poly(meth)acrylate polymer, EUDRAGIT® NE 30 D, is used in formulating the controlled release coating. EUDRAGIT® NE 30 D, RS 30 D and RL 30 D polymers are available from Rhom Pharma, D-6108 Weiterstadt 1, Dr. Otto-Rohm-Str. 2-4, Germany. EUDRAGIT® NE 30 D is a pH independent polymer available as a 30% or 40% aqueous dispersion. EUDRAGIT RS 30 D and RL 30 D are available as aqueous dispersions containing 30% dry substances.

The polymer is present in the controlled release coating mixture at an amount of from about 60 to about 80% based on total weight of the final, dried controlled release coating; preferably, at about 70 to about 79%; and most preferably, at about 77% of the total weight of the solids content of the controlled release coating. The release rate of the pharmaceutical agent from the pellets decreases when the content of polymer increases. Preferably, the polymer amount in the final layered and coated pellet is about 7 to about 10%, based on the total weight of the layered and coated pellet, and preferably 7.5–8.5% of the total weight of the layered and coated pellet.

The polymer dispersion is mixed with a suspension of lubricant/glidant agent, such as calcium stearate, magnesium stearate, zinc stearate, stearic acid or talc to form the controlled release coating mixture. The preferred lubricant/glidant is calcium stearate. The final, dried controlled release coating contains about 15 to about 40% calcium stearate or other lubricant/glidant agent, and most preferably about 20–23%, and most preferably about 23% calcium stearate based on the total weight of solids content of the controlled release coating. The lubricant/glidant functions to prevent agglomeration of the coated pellets during processing and also helps to delay release of the pharmaceutical agent from the coated pellets. The presence of an amount of about 20 to about 23% w/w calcium stearate in the outer controlled release coating results in delayed release of drug for about two hours following oral administration of the formulation.

The total amount of controlled release coating sprayed on the pharmaceutical loaded pellets may be varied depending on the desired release rate of the pharmaceutical agent. When the pharmaceutical agent of the pellets is nifedipine, it is preferred that the outer controlled release coating comprise about 5 to about 15% of the total weight of the pellet, and most preferably, about 10 to about 11.5% of the total weight of the pellet.

The pellet coatings may further contain pharmaceutically acceptable excipient such as fillers, anti-adherents, pharmaceutically acceptable pigment such as, titanium dioxide, iron oxide and various color pigments including vegetable dyes, and the like.

The first stage and second stage layerings and controlled release coating may be sprayed onto the pellets in a fluid bed apparatus is using a Wurster column, for example. Fluid-bed techniques are well known in the art and are readily applicable to production of controlled release coated particles.

After the pellets have been coated with first and second stage layers and outer controlled release coating, they are subjected to a curing process. The pellets are cured at a temperature in the range of from about 30° to about 50° C., preferably, from about 35° to about 45° C., and most preferably, about 40° C. for a period of about 5 to about 10 days and, preferably, about 7 days. Surprisingly, although others in the art have found shorter curing times to be preferred, we have found that these long curing times help to stabilize the release of pharmaceutical agent from the pellets even after long storage periods.

The cured coated pellets may be weighed out according to the total dose of pharmaceutical agent to be administered to patients. Diluent may be added, such as, for example, dextrose, sorbitol, mannitol, microcrystalline cellulose, methocel ether, lactose, glyceryl palmitostearate, glyceryl stearate, glyceryl behenate, and combinations thereof, among other commonly used pharmaceutical diluents, and the mixture of coated pellets and diluents pressed into tablets. Alternatively, the mixture or the coated pellets alone can be encapsulated in a hard gelatin capsule.

It is often desirable to add inert diluent when formulating the coated pellets into tablet form. The presence of pharmaceutical diluents, such as microcrystalline cellulose, methocel ether, glyceryl palmitostearate, glyceryl stearate, and/or glyceryl behemate, for example, in the pellet mixture serves to cushion the pellets so that they are not significantly ruptured during compression.

In general, the release rate of pharmaceutical agent from the pellets is dependent upon a number of factors including the potency of the layered pellets, the amount of surfactant present in the layers of the pellets, the type and amount of polymer present in the controlled release layer and the amount of controlled release coating applied. For example, the higher the potency of the pellets, the faster the release rate. Similarly, the higher the amount of surfactant in the pellet, the faster the release rate.

The process of the invention is particularly suitable for formulating a controlled release nifedipine formulation for once daily oral administration. Preferably the nifedipine formulation is composed of multi-layered pellets having a surfactant-containing innermost layer of nifedipine and binder, a second layer of nifedipine and binder and an outermost controlled release coating. The pellets are preferably formulated to provide a potency of about 40 to about 50%. The pellets may be formulated into tablets or encapsulated in the desired dosage amount. Typical unit dosage amounts for a once daily controlled release tablet of nifedipine for oral administration include any dosage between about 25 and 100 mg, such as 30, 60 and 90 mg. The nifedipine formulation of the invention is formulated to provide a pharmaceutically effective dosage of nifedipine at an approximately constant rate over an approximately 24 hour period.

The following examples are illustrative of the invention, and are not to be construed as limiting the invention.

EXAMPLE 1

PREPARATION OF NIFEDIPINE CONTROLLED RELEASE PELLETS

Drug layering of pellets was carried out in a two-stage operation as follows:
Step 1
  Non-pareil pellets 25/30 mesh 1000 g
  Nifedipine micronized 500 g
  Hydroxypropylmethyl 1250 g
  cellulose E-6 (HPMC) as 10% w/w solution in water
  Antifoam suspension 25 g
  Sodium lauryl sulfate (SLS) 12.5 g
  Deionized water 1250 g
The HPMC solution was mixed with one half the amount of water for about five minutes, after which the SLS and 12.5 g of the antifoam suspension and nefedipine were added. The mixture was homogenized in a Silverson homogenizer using an emulsifying head for about 15 minutes. The remainder of the water and antifoam suspension were added, and mixing at low speed was carried out for about 15 minutes using a stir-pak mixer. The mixture was sprayed onto the non-pareil pellets using a fluid-bed apparatus fitted with a Wurster insert.
Step 2
  Layered pellets from Step 1 800 g
  Nifedipine micronized 500 g
  HPMC as 10% solution in water 1250 g
  Antifoam suspension 25 g
  Deionized water 1250 g
The HPMC solution was mixed with one half of the water for about five minutes. One half of the antifoam suspension was added together with the nifedipine, and mixing was continued for about five minutes. The mixture was homogenized in a Silverson homogenizer with an emulsifying head for about 15 minutes. The remainder of the water and antifoam suspension were added, and the mixture was mixed at low speed for about 15 minutes. The mixture was sprayed onto the non-pareil pellets from Step 1 using a fluid bed apparatus fitted with a Wurster insert. The process was then repeated with another 800 g of pellets obtained from Step 1, using the same amounts of other ingredients as listed above.
  Controlled Release Coating
    Drug layered pellets from Step 2 1350 g (theoretical potency 51% w/w)
    EUDRAGIT NE 30 D 30% dispersion 750 g
    Calcium stearate suspension 15% w/w 450 g
Two identical batches of calcium stearate suspensions in water were first formed as follows. 5 g of antifoam suspension was mixed in 845 g of deionized water, after which 150 g of calcium stearate was added, and the resulting mixture was mixed well for ten minutes. After mixing, the two batches were combined and mixed for about five minutes. The solution was then homogenized in a Silverson homogenizer using an emulsifying head for 15 minutes.

The dispersion of EUDRAGIT® NE 30 D (750 g) was then added to the calcium stearate/antifoam suspension (450 g) and mixed for about 15 minutes at medium speed using a stir-pak mixer. The total dispersion was 1200 g.

720 g of the dispersion was then sprayed onto the drug-layered pellets from Step 2 using a fluid-bed apparatus fitted with a Wurster insert. This amount of coating provided a total outer coating of about 11.5% for a theoretical potency of 45.3%.
Curing
  Pellets obtained from the controlled release coating step were spread out on trays and heated in a forced air oven at a temperature of about 40° C. for seven days.

EXAMPLE 2

PREPARATION OF NIFEDIPINE CONTROLLED RELEASE PELLETS

Drug layering of pellets was carried out in a two-stage operation as follows:
Step 1
  Non-pareil pellets 25/30 mesh 1000 g
  Nifedipine micronized 500 g
  Hydroxypropylmethyl 1250 g
  cellulose E-6 (HPMC) as 10% w/w solution in water
  Antifoam suspension 25 g
  Sodium lauryl sulfate (SLS) 12.5 g Deionized water 1250 g The HPMC solution was mixed with one half the amount of water for about five minutes, after which the SLS and 12.5 g of the antifoam suspension and nefedipine were added. The mixture was homogenized in a Silverson homogenizer using an emulsifying head for about 15 minutes. The remainder of the water and antifoam suspension were added, and mixing at low speed was carried out for about 15 minutes using a stir-pak mixer. The mixture was sprayed onto the non-pareil pellets using a fluid-bed apparatus fitted with a Wurster insert.

Step 2
    Layered pellets from Step 1 800 g
    Nifedipine micronized 500 g
    HPMC as 10% solution in water 1250 g
    Antifoam suspension 25 g
    Deionized water 1250 g The HPMC solution was mixed with one half of the water for about five minutes. One half of the antifoam suspension was added together with the nifedipine, and mixing was continued for about five minutes. The mixture was homogenized in a Silverson homogenizer with an emulsifying head for about 15 minutes. The remainder of the water and antifoam suspension were added, and the mixture was mixed at low speed for about 15 minutes. The mixture was sprayed onto the non-pareil pellets from Step 1 using a fluid bed apparatus fitted with a Wurster insert. The process was then repeated with another 800 g of pellets obtained from Step 1, using the same amounts of other ingredients as listed above.

Controlled Release Coating
    Drug layered pellets from Step 2 900 g (theoretical potency 51% w/w)
    EUDRAGIT® NE 30 D 30% dispersion 500 g
    Calcium stearate suspension 15% w/w 300 g Two identical batches of calcium stearate suspensions in water were first formed as follows. 5 g of antifoam suspension was mixed in 845 g of deionized water, after which 150 g of calcium stearate was added, and the resulting mixture was mixed well for ten minutes. After mixing, the two batches were combined and mixed for about five minutes. The solution was then homogenized in a Silverson homogenizer using an emulsifying head for 15 minutes.

The dispersion of EUDRAGIT® NE 30 D (500 g) was then added to the calcium stearate/antifoam suspension (300 g) and mixed for about 15 minutes at medium speed using a stir-pak mixer. The total dispersion was 800 g.

408 g of the dispersion was then sprayed onto the drug-layered pellets from Step 2 using a fluid-bed apparatus fitted with a Wurster insert. This amount of coating provided a total outer coating of about 11%, to provide a polymer coating of 8.5% and a theoretical potency of 45.9%.

Curing

Pellets obtained from the controlled release coating step were spread out on trays and heated in a forced air oven at a temperature of about 40° C. for seven days.

EXAMPLE 3

FORMATION OF CONTROLLED RELEASE NIFEDIPINE TABLETS

Tablets were prepared from the pellets of Example 1 using a variety of presses set at various speeds and for various hardnesses. Prior to compressing, the pellets were combined with a suitable tablet matrix. Suitable matrices used to prepare nifedipine tablets of this invention include lactose, various grades of microcrystalline cellulose, various grades of methylcellulose, polyethylene glycol (PEG 8000), glyceryl palmitostearate, glyceryl stearate, glyceryl behenate, and combinations thereof.

EXAMPLE 4

FORMATION OF CONTROLLED RELEASE NIFEDIPINE CAPSULES

Capsules were prepared from the controlled release pellets of Example 1. About 155 mg of the pellets were weighed out and filled into Number 3 size hard gelatin capsules using an H&K capsule filling machine.

EXAMPLE 5

NIFEDIPINE RELEASE RATE FROM PELLETS UNDER DIFFERENT AGITATION CONDITIONS

Pellets used in this example were prepared as in Example 1.

Figure 1:
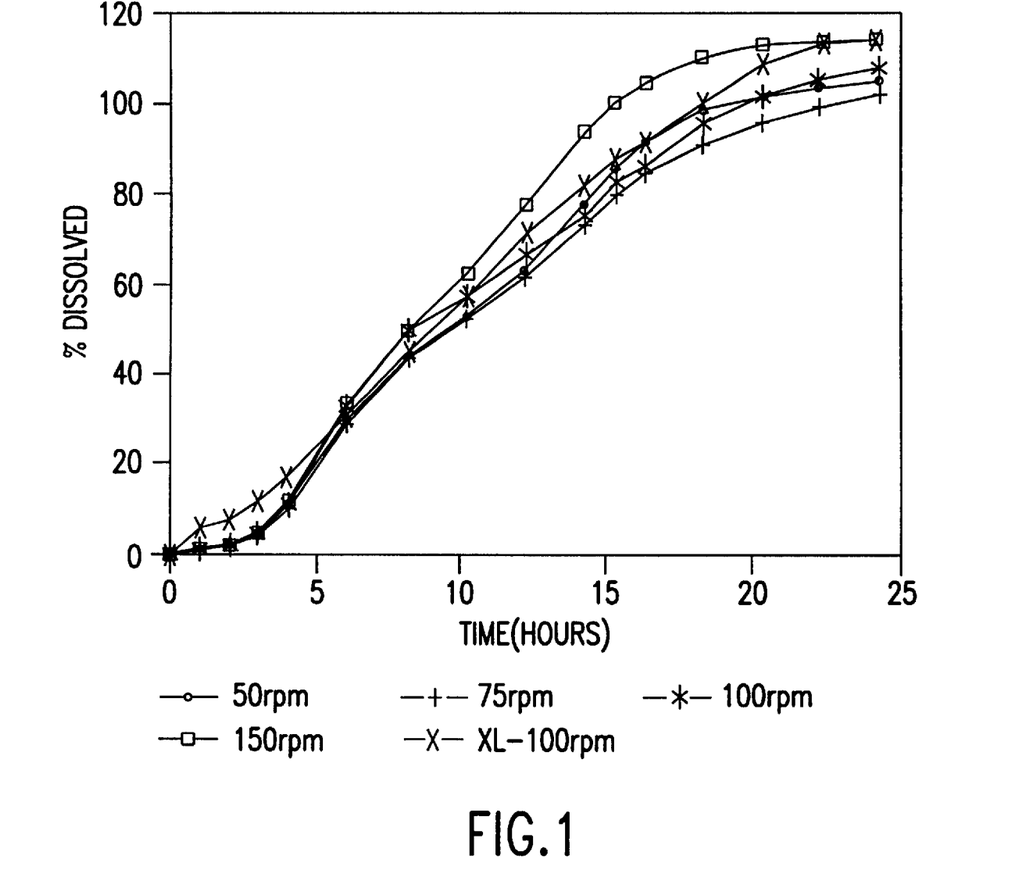
FIG. 1 is a graph of the in vitro release rate of nifedipine from pellets under different agitation conditions and the release rate from Procardia XL tablets at 100 rpm.

The pellets were tested for nifedipine release rates using USP apparatus II at various agitation speeds, i.e., 50, 75, 100 and 150 rpm for 24 hours. For comparative purposes, Procardia XL® tablets were tested at 100 rpm. Samples were removed periodically and the amount of nifedipine in solution was determined. The results are shown in FIG. 1.

These results show that the nifedipine release rate from the pellets is independent of rpm, and is very similar to the Procardia XL® release rate.

EXAMPLE 6

EFFECT OF CURING ON NIFEDIPINE RELEASE RATE

Pellets were prepared as described in Example 1, except that at the final step in the preparation, coated pellets were subjected to various curing (c) times at 40° C., i.e., 24 hours, 48 hours, and 7 days. One set of pellets was not cured at 40° C. (n) but was instead stored at room temperature (RT) for 7 days; another sample of pellets was stored under accelerated conditions (Acc.) for 7 days at 40° C. and 75% relative humidity.

Figure 2:
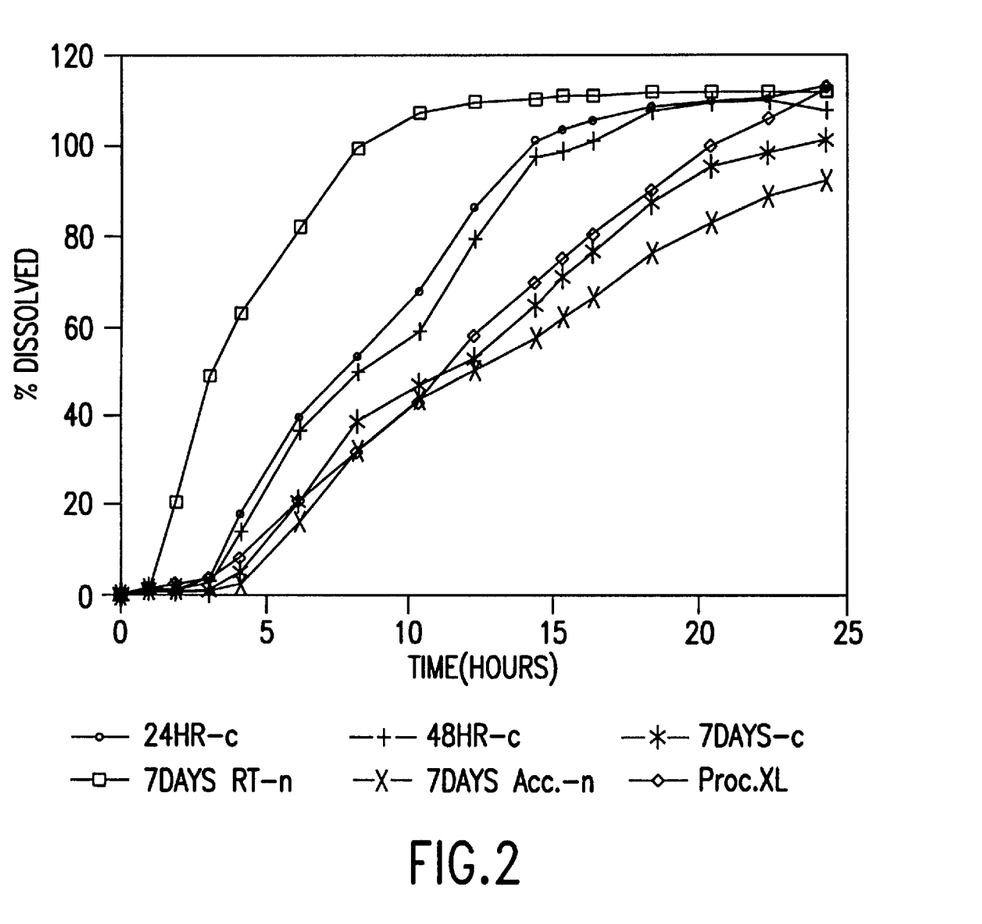
FIG. 2 is a graph of the in vitro release rate of nifedipine from pellets that have been cured at 40° C. for various lengths of time and from pellets that have not been cured.

The pellets were monitored to determine the effects of curing on in vitro drug release rates using USP Method II at 100 rpm. At various intervals samples were taken, and the percentage of dissolved nifedipine was determined. For comparative purposes, Procardia XL® tablets were also tested for release rates. The results are shown in FIG. 2.

The results indicate that increased curing time decreases the release rate of drug from the pellets. A curing time of 7 days at 40° C. appears to be preferred, as it provides a constant rate of release for about 22 hours following a delay of about two hours.

EXAMPLE 7

EFFECT OF SURFACTANT ON NIFEDIPINE RELEASE RATE

Pellets were prepared as described in Example 1, except that the amount of surfactant (SLS) and the location of surfactant (innermost drug layer versus outermost drug layer) was varied. The coated and cured pellets were tested for in vitro drug release using USP Method II, as described above. The SLS compositions of the pellets were as follows:

| Pellet No. | Amount and location of surfactant |
|---|---|
| A | 0.25× surfactant inner layer; 1.25× surfactant outer layer |
| B | 1× surfactant inner layer; 0 surfactant outer layer |
| C | same as B but with controlled release layer between surfactant layers |
| D | same as C but with 50% less controlled release layer between the surfactant layers |
| E | 0.5× surfactant distributed throughout matrix |
| F | 1.25× surfactant present in innermost layer |

The results of these experiments are shown in FIG. 3.

The results shown in FIG. 3 indicate that the presence of 1.25% surfactant in the innermost drug layer provides for a constant level release of nifedipine for a 22 hour period, following a delay of about two hours.

EXAMPLE 8

NIFEDIPINE RELEASE RATE FROM PELLETS

Pellets used in this example were prepared as in Example 2.

Figure 4:
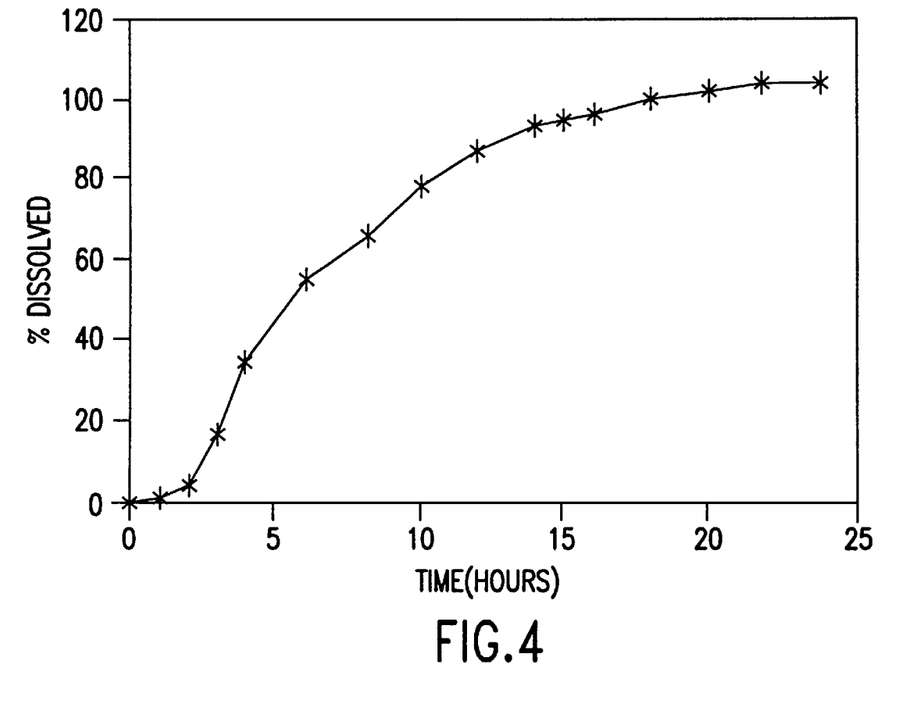
FIG. 4 is a graph of the in vitro release rate of nifedipine from pellets prepared as in Example 2.

The pellets were tested for nifedipine release rates using USP apparatus II at a speed of 100 rpm for 24 hours. Samples were removed periodically and the amount of nifedipine in solution was determined. The results are shown in FIG. 4.

EXAMPLE 9

TREATMENT OF ANGINA OR HYPERTENSION

Pellets are prepared as described in Example 1 or 2, compressed into tablet form by any of the methods of Example 3 or filled into hard gelatin capsules by the method of Example 4, and formulated to contain a dosage of nifedipine of 30 mg, 60 mg or 90 mg. These tablets or capsules are then administered orally to a patient suffering from angina, hypertension, or other disorder for which nifedipine is indicated. One tablet or capsule of appropriate dosage is administered to the patient on a daily basis until the medical condition being treated is cured, or until the symptoms are sufficiently relieved. This drug treatment may be continued indefinitely if needed to control or prevent disease symptoms.

What is claimed is:

1. A controlled release formulation comprising a pharmaceutically effective amount of nifedipine comprising:
   a non-pareil pellet having layered thereon
   (1) an innermost drug layer;
   (2) a second drug layer,
      wherein each of said drug layers comprises a pharmaceutically acceptable binder agent and nifedipine at a ratio of about 0.5 to 5 binder agent to nifedipine (w/w); and
   (3) an outermost controlled release coating comprising about 75 to about 80% of a water permeable polymer selected from the group consisting of a poly(meth)acrylate polymer, a copolymer of acrylic and methacrylic acid esters, and combinations thereof, (w/w) based on the total weight of the outermost coating and about 20 to about 25% lubricant/glidant agent, wherein the innermost drug layer, the second drug layer, or combination thereof further comprises a total amount of about 0.05 to about 5% surfactant (w/w) relative to the total amount of nifedipine present in the pellet; and wherein the formulation provides delayed release of nifedipine for about one to two hours followed by nifedipine release for about 22 hours.

2. The controlled release formulation of claim 1 wherein the innermost drug layer comprises from about 1.25 to about 3.0% surfactant based on the total amount of nifedipine present in the pellet.

3. The controlled release formulation of claim 2 wherein the surfactant is present in an amount of about 1.25% based on the total amount of nifedipine present in the pellet.

4. The controlled release formulation of claim 3 wherein surfactant is an ionic or non-ionic surfactant.

5. The controlled release formulation of claim 1 wherein the innermost drug layer and the second drug layer each contain about one half the amount of nifedipine present in the pellet.

6. The controlled release formulation of claim 1 wherein the non-pareil pellet has a mesh size in the range of from 14 to 60 mesh.

7. The controlled release formulation of claim 1 wherein the non-pareil pellet has a mesh size of from about 25 to about 30 mesh.

8. The controlled release formulation of claim 1 wherein the binder agent is hydroxypropylmethyl cellulose.

9. The controlled release formulation of claim 1 wherein the ratio of binder agent to nifedipine in each of the innermost drug layer and the second drug layer is about 1:4 (w/w).

10. The controlled release formulation of claim 1 wherein the pellet has a potency of about 40 to about 50% (w/w).

11. The controlled release formulation of claim 1 wherein the lubricant/glidant present in the controlled release coating is calcium stearate.

12. The controlled release formulation of claim 11 wherein the calcium stearate is present in an amount of about 23% based on the total weight of the controlled release coating.

13. The controlled release formulation of claim 1 wherein the controlled release coating comprises about 5 to about 15% of the total weight of the final pellet.

14. The controlled release formulation of claim 1 wherein the outermost controlled release coating comprises a copolymer of ethylacrylate and methylmethacrylate.

15. A method for treating angina or hypertension comprising administering an effective dosage amount of the controlled release formulation of claim 1 to a patient in need thereof.

16. The controlled release formulation according to claim 1 wherein said formulation is cured at a temperature in the range of from about 30° C. to about 50° C. for a period of from about 5 to 10 days.

17. The controlled release formulation according to claim 1 wherein said formulation is cured for about seven days at a temperature of about 40° C.

18. A controlled release formulation comprising a pharmaceutically effective amount of nifedipine comprising:
   a non-pareil pellet having layered thereon
   (1) an innermost drug layer comprising about 1.25% surfactant;
   (2) a second drug layer consisting essentially of binder and nifedipine,
      wherein each of said drug layers comprises a pharmaceutically acceptable binder agent and nifedipine at a ratio of about 0.5 to 5 binder agent to nifedipine (w/w); and
   (3) an outermost controlled release coating comprising about 70% of a polymer of poly(meth)acrylate, (w/w) based on the total weight of the outermost coating and about 25% calcium stearate, wherein the pellet provides an overall nifedipine potency of about 40 to about 50% and the formulation provides a delayed release of nifedipine for about one to two hours followed by nifedipine release for about 22 hours.

19. The controlled release formulation according to claim 18 wherein said formulation is cured at a temperature in the range of from about 30° C. to about 50° C. for a period of from about 5 to about 10 days.

* * * * *